United States Patent [19]
Ryden et al.

[11] Patent Number: 4,764,012
[45] Date of Patent: Aug. 16, 1988

[54] DEVICE FOR DETERMINING THE DISPLACEMENT OF A TOOTH BETWEEN TWO DIFFERENT EXAMINATIONS MADE ON SEPARATE OCCASIONS

[75] Inventors: Hans Ryden, Sturegatan 18, 11436 Stockholm; Hans Bjelkhagen, Stockholm, both of Sweden

[73] Assignee: Hans Ryden, Stockholm, Sweden

[21] Appl. No.: 579,284

[22] Filed: Feb. 14, 1984

Related U.S. Application Data

[63] Continuation of Ser. No. 287,582, Jul. 28, 1981, abandoned.

[51] Int. Cl.[4] ............................................. G01B 9/021
[52] U.S. Cl. ...................................... 356/347; 356/373
[58] Field of Search ............... 356/347, 348, 373, 375, 356/390, 394

[56] References Cited

U.S. PATENT DOCUMENTS

| | | | |
|---|---|---|---|
| 3,631,711 | 1/1972 | Kreuzer | 356/347 |
| 3,644,047 | 2/1972 | Brown et al. | 356/348 |
| 3,721,498 | 3/1973 | Narodny et al. | 356/394 |
| 3,744,911 | 7/1973 | Stetson et al. | 356/394 |
| 3,875,420 | 4/1975 | Ryden et al. | 250/578 |
| 3,975,101 | 8/1976 | Copeland | 356/394 |
| 3,976,383 | 8/1976 | Olsen | 356/394 |

OTHER PUBLICATIONS

Dirtoft et al., "Holographic Measuring of Deformations in Complete Upper Dentures", SPIE vol. 211, Optics and Photonics Applied to Medicine (1979), pp. 106–110.

*Primary Examiner*—R. A. Rosenberger
*Attorney, Agent, or Firm*—Burns, Doane, Swecker & Mathis

[57] ABSTRACT

A first photographic image (1) in the form of a hologram of the tooth (2) and location points (3) near the tooth taken on the occasion of the first examination is placed alongside a second photographic image (4') in the form of a hologram of the tooth (2') and location points (3') near the tooth taken on the occasion of the second examination. Adjusting devices (5, 6, 7) are provided to permit the displacement of the first photographic image (1) relative to the second photographic image (4'). This will bring the location points (3) on the first photographic image into line with the location points (3') on the second photographic image (4'), whereupon the displacement of the tooth (2) may be determined as the difference between the position of the tooth in the first photographic image (1) and the position of the tooth in the second photographic image (4').

10 Claims, 1 Drawing Sheet

DEVICE FOR DETERMINING THE DISPLACEMENT OF A TOOTH BETWEEN TWO DIFFERENT EXAMINATIONS MADE ON SEPARATE OCCASIONS

This application is a continuation of application Ser. No. 287,582, filed July 28, 1981 now abandoned.

TECHNICAL FIELD

The present invention relates to a device for determining the displacement of a tooth between two different examinations made on separate occasions, said device offering advantages in the area of orthodontics in that it presents a simple means of monitoring the displacement of the teeth during treatment.

DESCRIPTION OF THE PRIOR ART

Previously disclosed in American Patent Specification No. 3,875,420 is a method of using a device for determining the displacement of a tooth between two different examinations made on separate occasions.

This device is based on the principle of using a laser beam which is caused to be reflected from a special tooth surface and of analyzing the beam reflected in this way on a screen.

The displacement of the image of the tooth displayed on the screen between two examinations made on separate occasions thus provides an indication of the displacement of the tooth.

DESCRIPTION OF THE PRESENT INVENTION

Technical Problem

Although the principle of determining the displacement of a tooth between two different examinations made on separate occasions has, as such, already been disclosed in the aforementioned American Patent Specification, it is nevertheless apparent that the previously disclosed device requires a considerable quantity of apparatus to enable said determination to be made.

There is a great need to be able to determine such displacement by means of a very much more simple device, even though this could involve reduced accuracy.

There is a particular need to be able to make the determination in such a way that the displacement may be seen with the naked eye.

Solution

The present invention is intended to provide details of a device of such a nature that its use has made it possible to determine in a simple manner the displacement of a tooth between two different examinations made on separate occasions.

The invention is based on the principle of placing a first photographic image of the tooth and location points near the tooth taken on the occasion of the first examination alongside a second photographic image or model of the tooth and location points near the tooth taken on the occasion of the second examination.

The invention also includes details of a means enabling relative displacement to be produced between the first photographic image and the second photographic image or model. This displacement permits the fixed location points on the first photographic image to be brought into register with the corresponding location points on the second photographic image or on the model. Once these points are in register, it will then be possible to determine the displacement of a specific tooth as the difference between the position of the tooth in the first photographic image and the position of the tooth in the second photographic image or in the model.

The invention places particular emphasis on the requirement that the first photographic image shall be in the form of a hologram. This may, of course, also be the case for the second photographic image. The holograms may be taken from models of a jaw.

However, there is nothing to prevent the holograms from being produced by reproducing the position of the teeth directly in the mouth, for which purpose the previously disclosed method of producing a hologram by means of a laser beam is used.

By producing a photographic image of the tooth on the one hand and of location points near the tooth on the other hand, as directed, these location points may conveniently be in the form of adjacent teeth, preferably molars. In this way the location points may be regarded as being infinite in number, thus enabling the displacement of the tooth to be determined more precisely.

The present invention includes the possibility of causing the first and/or the second photographic image to be in the form of reflection holograms, preferably a white-light hologram. An example of this kind of hologram is the type known as the 'Lippmann' type.

By positioning a light-permeable filter between the first photographic image and the second photographic image, and above all between the first photographic image and the model, and by causing the first photographic image in the form of a hologram to be bleached so as to increase its light-permeability, the result will be a matching of the light intensity of the first photographic image to that of the model on the one hand and on the other hand the creation of a state of interference for the tooth which has been displaced and which accordingly will have assumed different positions in the image and in the model.

This interference clearly reveals the actual displacement of the tooth.

Finally, the utilization of holograms offers the advantage that the displacement may be determined not only in a single plane, but also three-dimensionally, which requires that the displacement of the images relative to each other must be provided by means of three adjusting devices situated on perpendicular coordinates.

Advantages

The principal advantages associated with the device in accordance with the present invention are that it has succeeded in resolving the technical problems indicated above, at the same time as the apparatus used is simple and produces measurement results well within acceptable tolerances.

The measurement result may be appreciated rapidly with the naked eye, and in certain cases the hologram may make the complicated process involved in producing the model entirely superfluous.

Finally, holograms permit the difference to be determined three-dimensionally.

DESCRIPTION OF THE DRAWINGS

Two preferred embodiments of a device for determining the displacement of a tooth between two different examinations made on separate occasions which exhibits the significant characteristics of the present invention will be described in greater detail with reference to the attached drawing, in which.

DESCRIPTION OF THE PREFERRED EMBODIMENTS

Figure 1:
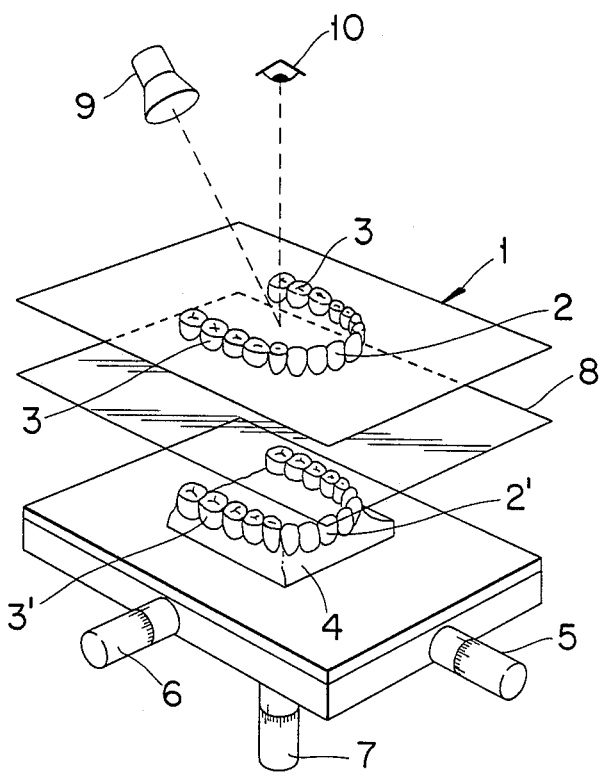
FIG. 1 is a perspective view of the basic arrangement of the first embodiment of the device in accordance with the present invention, from which certain component parts have been omitted in the interests of clarity.

With reference to the attached drawing, FIG. 1 shows a prespective view of a device for determining the displacement of a tooth between two different examinations made on separate occasions. The time between the two occasions may be several weeks, several months, or even several years.

The invention makes use of a first photographic image 1. The image contains the tooth of which it is wished to determine the displacement. This tooth has been allocated the reference designation 2. The photographic image 1 must also contain location points 3 adjacent to the tooth 2. These location points are shown as being molars, which may be taken as an indication that the location points are infinite in number. Thus the photographic image 1 represents the actual tooth and the teeth adjacent to it on the occasion of the first examination.

The device in accordance with the present invention offers the possibility of placing a model 4 alongside the first photographic image 1, said model showing the tooth 2' and the location points 3' adjacent to that tooth. The purpose of the model is to illustrate the position of the tooth on the occasion of the second examination.

Figure 2:
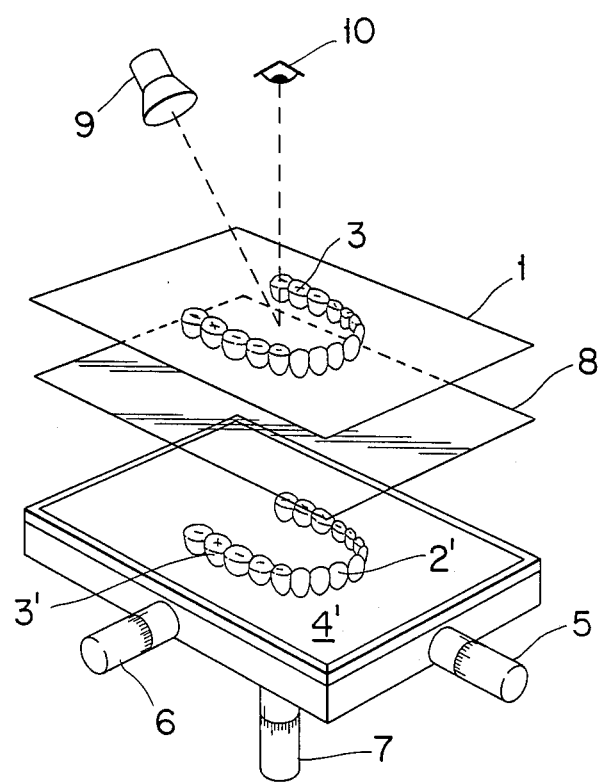
FIG. 2 shows a perspective view of the basic arrangement of the second embodiment of the device in accordance with the present invention, from which certain component parts have been omitted in the interests of clarity.

Although the embodiment in accordance with FIG. 1 shows a model of the tooth and the location points adjacent to the tooth on the occasion of the second examination, there is nothing to prevent the use of a second photographic image 4' to represent the position of the tooth on the occasion of the second examination in accordance with FIG. 2.

The device in accordance with the present invention includes adjusting means or devices with the reference designations 5, 6 and 7, designed to permit relative displacement to be produced between the first photographic image 1 and the model 4 or the image 4' so as to bring the location points 3 in the first photographic image 1 into register with the location points 3' in the model 4 or in the second photographic image 4'. The displacement of the tooth 2 from the position 2 to the position 2' may be determined as the difference between the position of the tooth in the first photographic image and the position of the tooth in the model or in the second photographic image.

The particular purpose of the present invention is to cause the first photographic image 1 to be in the form of a hologram. It will also be found to be convenient to cause not only the first but also the second image to be in the form of a hologram taken directly inside the mouth.

The problem of achieving precise location points has been eliminated in accordance with the present invention by totally avoiding the use of marked location points and by using adjacent teeth as the location points, these being preferably molars, which will not be displaced by any orthodontic treatment of an incisor.

The first and/or the second image is in the form of a reflection hologram, preferably a white-light hologram, for instance of the kind known as the 'Lippmann' type.

The present invention also includes a light-permeable filter 8, which must be placed between the first photographic image 2 and the second photographic image 4' or the model 4. The filter is intended to be used in the event of a model made from white plaster being used.

In accordance with the present invention, the first photographic image in the form of a hologram should preferably be bleached, permitting the light-permeable filter to be positioned so that on the one hand the light intensity of the first photographic image is matched to that of the model, and so that on the other hand a clearly distinguishable interference will be produced showing the changed position of the tooth, i.e. its displacement.

The means or adjusting devices identified by the reference designations 5, 6 and 7 for producing the displacement of the images relative to each other consist on the one hand of the organs 5 and 6 for producing the displacement with the distance between the images remaining constant, and on the other hand of the organ 7 for producing said displacement by varying the distance between the images, i.e. providing a three-dimensional displacement facility.

In order to permit the photographic image 1 together with its integral hologram to be viewed, the present invention includes a lamp 9 of the spotlight type. This is positioned in such a way as to cause the rays of light to fall upon the photographic image 1 at an angle of incidence which will cause the hologram to be recreated precisely.

This angle must be the same as the angle of the laser beam used to etch the hologram image. An eye 10 intended to look at the photographic image 1 and to compare it to the photographic image 4' or model 4 placed beneath it shall be positioned directly above the image as shown in the attached drawing in FIG. 1.

The filter 8 is designed so as to be capable of regulating the light reflected from the model at a level of intensity essentially corresponding to the intensity of the light transmitted through the hologram image of the first photographic image 1. The use of a polarized filter may be appropriate here.

The aforementioned means or adjusting devices 5, 6 and 7 will benefit from being in the form of micrometer threads or servomotors connected to digital instruments. It is also possible to connect these devices to a computer and to determine the results of measurement in this way. In this case the procedure for the determination of the results of measurements will consist of first setting the location points 3 in relation to the location points 3' in such a way that the photographic image 1 and the model 4 or the photographic image 4' are located directly above each other. It is at this point that one may expect to see a change in position, or a displacement, between the tooth 2 and the tooth 2'. It will then be possible with the help of the adjusting device 5, for instance, to displace the photographic image 4' so that the tooth 2' moves to a position directly below the tooth 2. The displacement produced in this way by the adjusting device 5 will also be the displacement of the tooth 2 between the two examinations.

The present invention makes it especially convenient to compare one hologram 1 to another hologram 4', as shown in FIG. 2.

The filter has two different functions. A filter may be used to give the model 4 a green colour. If the hologram 1 exhibits a red image, then this will produce a difference in colour (an interference) which will be easily distinguishable in respect of the displacement of the tooth. The filter is also used to match the intensity of the light reflected from the model 4 or from the second photographic image 4' to the intensity of the light reflected from the first photographic image 1. It may be appropriate in this connection to bleach the hologram of the first photographic image.

The hologram for the entire set of teeth will contain stored information in respect of the relative positions of the teeth and may make plaster impressions unnecessary in certain circumstances.

The present invention is not restricted to the typical embodiments described above, but may undergo modifications within the scope of the idea of invention.

It should be pointed out that the attached drawing does not show the necessary retaining device for the image 1, the filter 8 and the supporting surface for the adjusting devices 5, 6 and 7. These have also been illustrated in an exploded view in the interests of clarity. These components must be positioned directly adjacent to each other when determining the displacement.

We claim:

1. A device for determining the displacement of a tooth between two different examinations made on separate occasions, comprising a first photographic image of the tooth containing location points near the tooth taken on the occasion of the first examination, said first photographic image being in the form of a hologram, said first photographic image being placed alongside a second representation of the tooth having location points near the tooth taken on the occasion of a second examination, said location points on the first photographic image and the second representation being teeth adjacent said tooth, means for displacing the first photographic image relative to said second representation to move the location points on the first photographic image into correspondence with the location points on said second representation such that the displacement of the tooth is determined as the difference between the position of the tooth in the first photographic image and the position of the tooth in said second representation.

2. The device in accordance with claim 1, wherein at least one of the first photographic image and the second representation is in the form of hologram taken from a model of a jaw.

3. The device in accordance with claim 1, wherein at least one of the first photographic image and the second representation is in the form of a hologram taken directly inside the mouth.

4. The device in accordance with claim 1, wherein the adjacent teeth are molars.

5. The device in accordance with claim 1, wherein at least one of the first photographic image and the second representation is in the form of a reflection, white-light hologram.

6. The device in accordance with claim 1, further comprising a light-permeable filter arranged between the first photographic image and said second representation.

7. The device in accordance with claim 1, wherein the first photographic image in the form of a hologram is bleached and further comprising a filter arranged to match the light intensity of the first photographic image to that of the second representation and to produce interference indicating the displacement of the tooth.

8. The device in accordance with claim 1, wherein the means for displacing the first photographic image relative to said second representation comprises devices for producing said displacement with the distance between the first photographic image relative to said second representation remaining constant and a device for varying the distance between the first photographic image and said second representation such that three-dimensional displacement of the first photographic image and said second representation is permitted.

9. The device in accordance with claim 1, wherein said second representation is a second photographic image.

10. The device in accordance with claim 1, wherein said second representation is a model.

* * * * *